US012622604B2

(12) United States Patent
Devani

(10) Patent No.: US 12,622,604 B2
(45) Date of Patent: May 12, 2026

(54) SYSTEMS AND METHODS FOR MONITORING MOVEMENTS

(71) Applicant: BioTrillion, Inc., San Francisco, CA (US)

(72) Inventor: Savan R. Devani, San Francisco, CA (US)

(73) Assignee: BioTrillion, Inc., San Francisco, CA (US)

( * ) Notice: Subject to any disclaimer, the term of this patent is extended or adjusted under 35 U.S.C. 154(b) by 929 days.

(21) Appl. No.: 17/614,262

(22) PCT Filed: May 29, 2020

(86) PCT No.: PCT/US2020/035265
§ 371 (c)(1),
(2) Date: Nov. 24, 2021

(87) PCT Pub. No.: WO2020/243531
PCT Pub. Date: Dec. 3, 2020

(65) Prior Publication Data
US 2022/0248980 A1      Aug. 11, 2022

Related U.S. Application Data

(60) Provisional application No. 62/855,725, filed on May 31, 2019.

(51) Int. Cl.
*A61B 5/11*          (2006.01)
*A61B 5/00*          (2006.01)
(52) U.S. Cl.
CPC .......... *A61B 5/1114* (2013.01); *A61B 5/1123* (2013.01); *A61B 5/1126* (2013.01);
(Continued)

(58) Field of Classification Search
CPC ........... G06N 3/09; A61B 5/11; A61B 5/1113; A61B 5/1116; A61B 5/1118;
(Continued)

(56) References Cited

U.S. PATENT DOCUMENTS 8,843,101 B2    9/2014  Fish
9,060,714 B2    6/2015  Bajcsy
(Continued)

FOREIGN PATENT DOCUMENTS

CN      111199165 A      5/2020
WO      2020157746 A1    8/2020
WO      2021195316 A1    9/2021

OTHER PUBLICATIONS

M. Stikic and B. Schiele, "Activity Recognition from Sparsely Labeled Data Using Multi-Instance Learning," 2009, Springer, Berlin, Heidelberg; Location and Context Awareness. LoCA 2009. Lecture Notes in Computer Science, vol. 5561. (Year: 2009).*
International Search Report and Written Opinion in International Patent Application No. PCT/US2020/035265, mailed Nov. 23, 2020 (12 pages).
Supplementary European Search Report mailed May 10, 2023 in EP 20815469.0 (7 pages).
(Continued)

*Primary Examiner* — Tse W Chen
*Assistant Examiner* — Alice Ling Zou
(74) *Attorney, Agent, or Firm* — Nixon Peabody LLP

(57) ABSTRACT

Disclosed are systems and methods for classifying body movements, including gestures and activities of daily living. This may include preprocessing data output from an accelerometer and gyroscope into features that are input into a movement classifier. In some examples, the disclosed technology may utilize user confirmed labels of movements to improve the accuracy of the movement classifiers. This may include providing a notification to a user when a movement classifier determines a particular movement is detected that requests confirmation of the movement label.

20 Claims, 8 Drawing Sheets

Accuracy of the model when training dataset is enhanced by x user-labelled sessions for each ADL

(52) U.S. Cl.
CPC .......... *A61B 5/6802* (2013.01); *A61B 5/7267*
(2013.01); *A61B 2562/0219* (2013.01)

(58) Field of Classification Search
CPC ................ A61B 5/1123; A61B 5/1126; A61B
5/7264–7267; A61B 2562/0219; G16H
50/20
See application file for complete search history.

(56) References Cited

U.S. PATENT DOCUMENTS

| | | | |
|---|---|---|---|
| 10,614,303 B2 | 4/2020 | Klingström | |
| 11,109,015 B2 | 8/2021 | Iwasaki | |
| 2012/0116187 A1* | 5/2012 | Hayes | A61B 5/7264 |
| | | | 600/587 |
| 2013/0190903 A1 | 7/2013 | Balakrishnan | |
| 2014/0350436 A1 | 11/2014 | Nathan | |
| 2015/0066422 A1* | 3/2015 | Zhang | A61B 5/1126 |
| | | | 702/141 |
| 2016/0327397 A1 | 11/2016 | Cordova | |
| 2017/0010663 A1 | 1/2017 | Tanaka | |
| 2017/0103178 A1* | 4/2017 | Heinrich | G16H 50/30 |
| 2017/0124480 A1 | 5/2017 | Sarkar | |
| 2017/0182362 A1* | 6/2017 | Mcleod | A61B 5/0002 |
| 2017/0196497 A1 | 7/2017 | Ray | |
| 2018/0221237 A1* | 8/2018 | Swift | A61H 3/00 |
| 2020/0218974 A1* | 7/2020 | Cheng | G06N 3/044 |
| 2020/0251190 A1 | 8/2020 | Glasner | |
| 2020/0364868 A1 | 11/2020 | Zhang | |
| 2024/0420290 A1 | 12/2024 | Vatanparvar | |

OTHER PUBLICATIONS

Sztyler, et al., "Online Personalization of Cross-Subjects Based Activity Recognition Models on Wearable Devices," 2017 IEEE International Conference on Pervasive Computing and Communications (PerCom), IEEE, Mar. 13, 2017, 180-189 (10 pages).

Stikic, et al., "Exploring Semi-Supervised and Active Learning for Activity Recognition," 2008 ISWC, 12th IEEE International Symposium on Wearable Computers, Sep. 1, 2008, 81-88 (8 pages).

Shahmohammadi, et al., "Smartwatch Based Activity Recognition Using Active Learning," 2017 IEEE/ACM International Conference on Connected Health: Applications, Systems and Engineering Technologies (CHASE), Jul. 1, 2017, 321-329 (9 pages).

Guoen Cai, Zhirong Lin, Houde Dai, Xuke Xia, Yongsheng Xiong, Shi-Jinn Horng, Tim C. Lueth, Quantitative assessment of parkinsonian tremor based on a linear acceleration extraction algorithm, Biomedical Signal Processing and Control, vol. 42, 2018, pp. 53-62, ISSN 1746-8094, https://doi.org/10.1016/j.bspc.2018.01.008.

Bazgir O, Habibi SAH, Palma L, Pierleoni P, Nafees S. A classification system for assessment and home monitoring of tremor in patients with Parkinson's disease. J Med Signals Sens. 2018;8(2):65, 10.4103/jmss.JMSS_50_17.

Wang, X., Garg, S., Tran, S.N. et al. Hand tremor detection in videos with cluttered background using neural network based approaches. Health Inf Sci Syst 9, 30 (2021). https://doi.org/10.1007/s13755-021-00159-3.

Ferenčík, N.; Jaščur, M.; Bundzel, M.; Cavallo, F. The Rehapiano—Detecting, Measuring, and Analyzing Action Tremor Using Strain Gauges. Sensors 2020, 20, 663. The Rehapiano—Detecting, Measuring, and Analyzing Action Tremor Using Strain Gauges.

* cited by examiner

Figure 7:
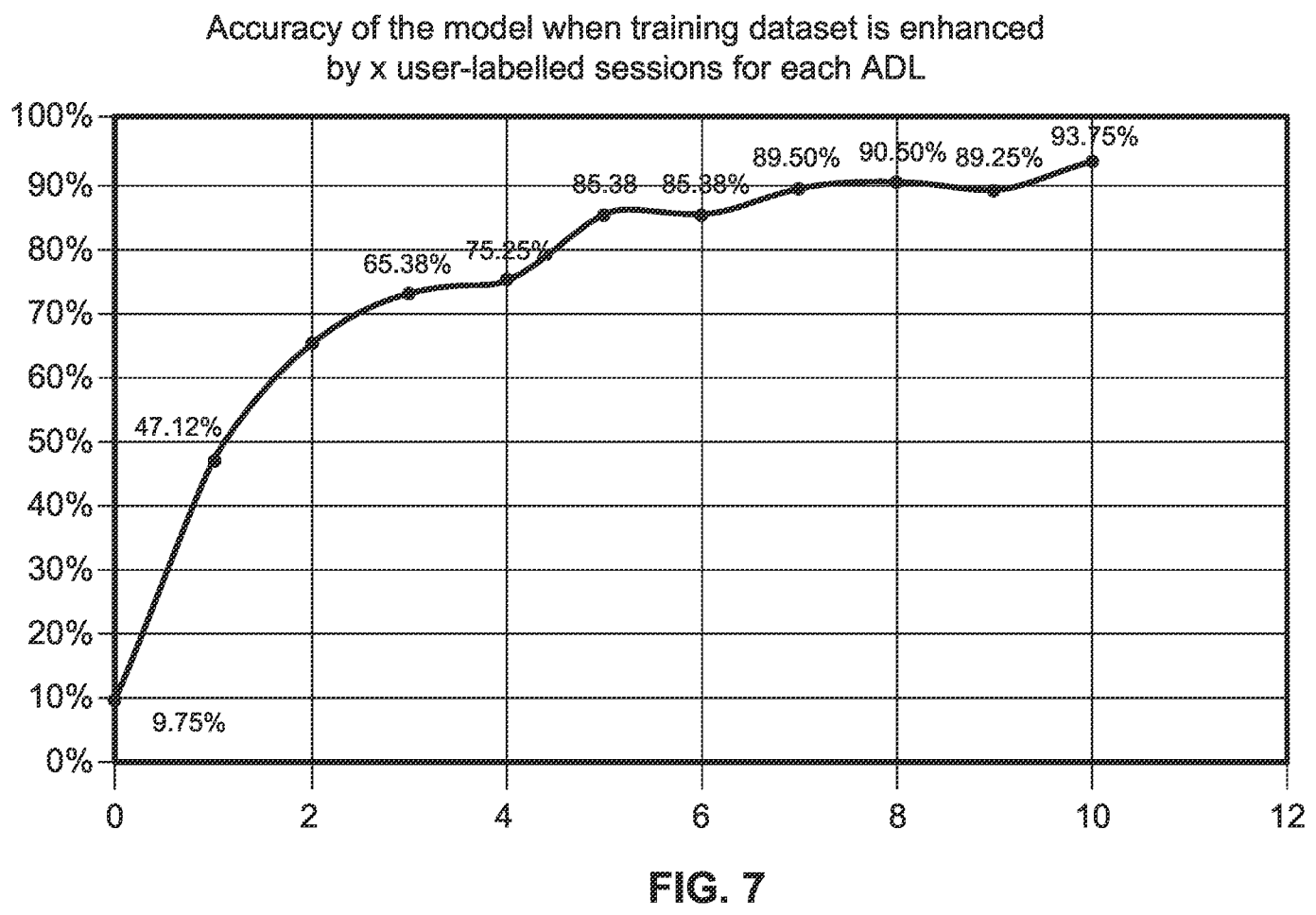

Accuracy of the model when training dataset is enhanced by x user-labelled sessions for each ADL 93.75%

ADLs that involve only cyclical hand movement

ADLs that involve only non-cyclical hand movement

SYSTEMS AND METHODS FOR MONITORING MOVEMENTS

CROSS-REFERENCE TO RELATED APPLICATIONS

This application is a U.S. National Stage of International Application No. PCT/US2020/035265, filed May 29, 2020 which claims priority to and the benefit of U.S. Provisional Application No. 62/855,725 filed May 31, 2019, titled HAND KINETIC VECTOR INFERRED GESTURES TO CLASSIFY ACTIVITIES OF DAILY LIVING, each of which is hereby incorporated herein by reference in their entireties.

FIELD

The present invention is directed to systems and methods for monitoring movements, including classification of movements based on data output from wearables.

BACKGROUND

The following description includes information that may be useful in understanding the present invention. It is not an admission that any of the information provided herein is prior art or relevant to the presently claimed invention, or that any publication specifically or implicitly referenced is prior art.

Users perform a variety of movements and gestures throughout their lives, including in performing their daily activities. Identifying, tracking and monitoring these movements can provide useful information about a user.

SUMMARY

Specific or repeated body movements that can be passively and objectively classified have the potential to provide insights into the existence of certain conditions, diseases and/or disorders of a user. For example, anorexia, depression, anxiety, and/or other diseases, disorders and conditions may be inferred from repeated, particularly cyclic, motions. Similarly, behaviors that may lead to diseases, such as smoking, may be inferred from repeated hand motions. Such data may also be combined with other forms of context-based metadata such as time of day, or the amount of time a touch screen is active in order to improve the classification accuracy of such behaviors, or put them into more meaningful context.

For instance, the disclosed systems and methods may aid in compliance with prescribed diabetes management, including by monitoring aspects of eating such as frequency, duration, time of day. Metabolic, endocrine, hormonal diseases and disorders or conditions like pregnancy might also be classified with non-binary statistical probability based on changes in behaviors inferred from a user's kinetic body or hand activity.

Additionally, certain digestive diseases/disorders such as irritable bowel syndrome (IBS) might be detected based on the monitoring of eating movements of a user as described herein and any statistically significant changes to established homeostatic baselines related thereto. Side-effects/adverse-events in response to novel drug treatments in clinical trials may also be determined based on detection of particular hand motions as described above.

Further, weight gain/loss, changes in health or lifestyle, and/or habits (such as binge eating, eating small bites through the day, or sleeping right after eating) might be inferred based on the behaviors indicated by the hand motion detected. A corresponding alert and/or other applications can be provided based on the activities inferred from the hand motions. Depression, pregnancy, sleep disorders, the risk of certain obesity related disease such as diabetes might also be indicated in the alert.

Detection and/or prediction of conditions, disorders and/or diseases noted above may serve as an indication of holistic health, providing insights into the multiple facets of disease risk, and/or may be usable in assisting individuals to alter their behaviors. Insurance companies might adopt smart device-derived next-gen metrics akin to "steps" into their risk stratification, but there are many other ways to stratify risk (such as frequency of eating as an "inverse" corollary of steps). Changes in baseline behavior or emergence of novel hand gestures (e.g. tremors) may serve as indications of potentially serious side effects in patients in drug trials. Conversely, reduction in similar motions may prove evidence of efficacy when targeting diseases, disorders and/or conditions.

The methods and systems described herein, in some examples, employ user-feedback to label movements. The system monitors sensors data output by inertial measurement unit(s) ("IMU"—a combination of at least one accelerometer and at least one gyroscope) and applies classifiers to the data to determine whether they are likely associated with a particular movement. In some examples, the system may monitor the sensor data and request confirmation from a user that a particular movement has been performed to label the ground truth of the data. These labels allow for the supervised training of software to passively detect similar movements, providing views into movement/gesture patterns and frequency specific to the user. These movements correspond to certain behaviors or activities of daily living ("ADLs") which affect health. Changes to baseline behaviors provide insights into changes in user health.

Health Applications

The method and system described herein may aid user health in a variety of applications. As an example, the methods and systems disclosed herein may be applied towards the following, which are non-comprehensive:

Detection of Smoking: detection of smoking patterns for the evaluation of cessation attempts;

Detection of Eating: monitoring of frequency/duration/time of day of eating motions as an indication of dietary-related effects in health (for example with applications towards diabetes, obesity, anorexia, etc.)

Detection of Complex Motor Functions: detecting problems with neuro-motor tasks as an indication of motor apraxia or neurodegenerative diseases (e.g. routine daily buttoning of shirt)

Detection of Urination: monitoring of changes in frequency and associated diseases/disorders/conditions such as renal or prostate disease.

Clinical Use Cases

Similarly, the method and system may have a number of clinical use cases such as the following examples.

The systems and methods may be used for detection of certain disorders that manifest through specific or repeated hand motions (e.g. anorexia, depression, anxiety, etc.). For example, if a user eats less frequently per day over time (anorexia) with other markers to bolster the statistical significance of this determination; Slowing of hand gestures (potential low weighted marker for depression); increasing speed of hand gestures (quantifiable data can be used to aid in the existence or risk of anxiety or other highly stimulated behavioral conditions).

The systems and methods may be used to monitor compliance with prescribed diabetes management (clinician-patient protocol and set of administered guidelines to follow that can be monitored through out-of-clinic continuous monitoring via smart wearable devices, that monitor eating (food intake) for example.

The systems and methods may be used to monitor meta-bolic/endocrine/hormonal diseases and disorders and/or conditions such as pregnancy. Metabolism is linked to energy, which tends to affect speed of hand/body kinetics. This alone would be a low weighted input in identifying such a disease/disorder/condition. In conjunction with changes in time/frequency, the markers may in summation correlate with (for example) changes in eating regularity caused by pregnancy. These would be coupled with other non-kinetic markers such as basal body temperature, behavioral changes, etc., to be able to make a determination as to the possible presence of the disease, disorder or condition.

The systems and methods may be used to monitor certain digestive diseases/disorders like irritable bowel syndrome (IBS). Hand kinetics can, through classification of complex motions (which undergo a cyclical pattern that can be used to train a universal algorithm), infer frequency of certain hand pattern associated with toilet use.

The systems and methods may be used to predict side-effects/adverse-events in response to novel drug treatments in clinical trials. Statistically significant changes to estab-lished movements normal for a particular individual may indicate issues. For example, a novel drug in phase III trials starts to cause changes in any one of the movements/gestures/behaviors/ADLs that are being passively and auto-matically classified. Increases or decreases in frequency, speed or time of day, of movements (e.g. eating, smoking, other ADLs) may be indicative of a medical issue, in which clinical advice would be a likely next-step. Statistical sig-nificance can be analyzed by categorizing the change in movement measured parameters relative to a low, medium and high risk. For example, "high risk" would describe movement classifications that were highly statistically vari-ant from established baseline levels for the individual, with "medium risk" being moderately statistically variant. Such measures of variance would be probabilistic-based by using standard deviation thresholds.

The systems and methods may be used to predict weight gain or loss (e.g. based on eating detection); changes in health or lifestyle based on behaviors (e.g. does someone binge eat, or eat small bites through the day, or sleep right after eating? Could these be associated with depression, pregnancy, sleep disorders, etc.), and the risk of certain obesity related diseases such as diabetes.

The systems and methods may be used to provide payer risk stratification. Detection/prediction of diseases, disorders and/or conditions noted above may serve as an indication of holistic health, providing insights into the multiple facets of disease risk. Payers such as insurance companies may adopt smart device-derived metrics into their risk stratification, such as frequency of eating as a marker of increased risk. The method and system may be used as an indicator of pharma efficacy or toxicity. Changes detected in baseline behavior or detection of the emergence of novel hand gestures (e.g. tremors) may serve as indications of poten-tially serious side effects in patients in drug trials. Con-versely, reduction in similar motions may prove evidence of efficacy when targeting diseases, disorders and/or conditions

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 7 is a line graph illustrating the overall accuracy improvement of classifiers trained with user labeled ses-sions.

FIG. 8A illustrates classifiers trained to identify cyclical movements that only involve the hand. FIG. 8B illustrates classifiers trained to identify non-cyclical move-ments that only involve the hand. FIGS. 8C and 8D illustrate classifiers trained to identify movements that involve the whole body.

Figure 1A:
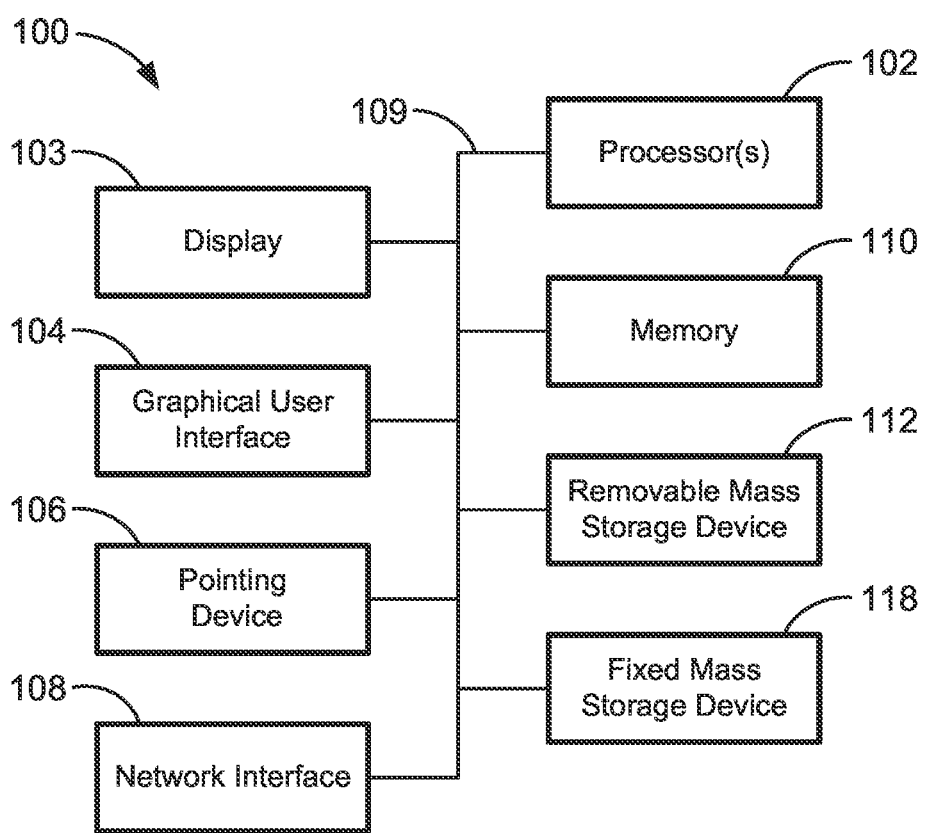
FIG. 1A is a block diagram of one embodiment of a computer system usable in a system for detecting gestures for classifying movements.

In the drawings, the same reference numbers and any acronyms identify elements or acts with the same or similar structure or functionality for ease of understanding and convenience. To easily identify the discussion of any par-ticular element or act, the most significant digit or digits in a reference number refer to the Figure number in which that element is first introduced.

DETAILED DESCRIPTION

Unless defined otherwise, technical and scientific terms used herein have the same meaning as commonly under-stood by one of ordinary skill in the art to which this invention belongs. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be under-stood as being modified by the term "about."

Definitions

As used herein, the term "movement" refers broadly to movements of the body, including the whole body or any part of the body including the arms, hands, head, legs, etc. Additionally, "movement" encompasses simple, discrete movements; gestures; complex behaviors, ADLs, and may include: smoking, eating, urinating, complex motor movements, standing up, laying down, eating with hands, eating with fork and knife, eating with a spoon, drinking, lying down from sitting, sitting up in bed, standing up from sitting, walking, running, typing on a keyboard, writing, washing hands, brushing teeth, climbing stairs, descending stairs, shaking head, sign language, and others as would be contemplated by those of skill in the art.

System Overview

FIG. 1A is a block diagram of one embodiment of a computer system 100 usable in a system for detecting gestures for classifying movements/gestures/behaviors such as ADLs. Other computer system architectures and configurations can be used for carrying out the processing of the disclosed technique. Computer system 100, made up of various subsystems described below, includes at least one microprocessor subsystem (also referred to as a central processing unit, or CPU) 102. For example, processor 102 can be implemented by a single-chip processor or by multiple processors. Processor 102 may have multiple cores in some embodiments. In some embodiments processor 102 is a general purpose digital processor which controls the operation of the computer system 100. Using instructions retrieved from memory 110, processor 102 controls the reception and manipulation of input data, and the output and display of data on output devices. In some embodiments, processor 102 includes and/or is used to provide functions described below. In some embodiments, processor 102 may be considered to include a neural network or other platform usable in deep learning.

Processor 102 is coupled bi-directionally with memory 110 which can include a first primary storage, typically a random-access memory (RAM), and a second primary storage area, typically a read-only memory (ROM). Primary storage can be used as a general storage area and as scratch-pad memory, and can also be used to store input data and processed data. Primary storage can also store programming instructions and data, in the form of data objects and text objects, in addition to other data and instructions for processes operating on processor 102. Primary storage typically includes basic operating instructions, program code, data and objects used by processor 102 to perform its functions (e.g., programmed instructions). For example, memory 110 may include any suitable computer-readable storage media, described below, depending on whether, for example, data access needs to be bi-directional or unidirectional. Processor 102 can also directly and very rapidly retrieve and store frequently needed data in a cache memory (not shown).

A removable mass storage device 112 provides additional data storage capacity for the computer system 100, and is coupled either bi-directionally (read/write) or uni-directionally (read only) to processor 102. Storage device 112 may also include computer-readable media such as magnetic tape, flash memory, signals embodied on a carrier wave, PC-CARDS, portable mass storage devices, holographic storage devices, and other storage devices, either local or remote. A fixed mass storage device 118 can also provide additional data storage capacity. The most common example of mass storage is a hard disk drive. Mass storage devices at 112 and 118 generally store additional programming instructions, data, and the like that typically are not in active use by processor 102. It will be appreciated that the information retained within mass storage devices 112 and 118 may be incorporated, if needed, in standard fashion as part of memory 110 (e.g. RAM) as virtual memory.

In addition to providing processor 102 access to storage subsystems, bus 109 can be used to provide access other subsystems and devices as well. In the described embodiment, these can include a display 103, a graphical user interface 104, a pointing device 106, and a network interface 108, as well as an auxiliary input/output device interface, a sound card, speakers, and other subsystems as needed. The pointing device 106 may be a mouse, stylus, track ball, or tablet, and is useful for interacting with graphical user interface 104.

The network interface 108 allows processor 102 to be coupled to another computer, computer network, or telecommunications network using a network connection as shown. Through the network interface 108, it is contemplated that the processor 102 might receive information (e.g., data objects or program instructions) from another network, or might output information to another network in the course of performing the above-described method steps. Information, often represented as a sequence of instructions to be executed on a processor, may be received from and outputted to another network, for example, in the form of a computer data signal embodied in a carrier wave. An interface card or similar device and appropriate software implemented by (e.g. executed or performed on) processor 102 can be used to connect computer system 100 to an external network and transfer data according to standard protocols. For example, various process embodiments disclosed herein can be executed on processor 102, or can be performed across a network such as the Internet, intranet networks, or local area networks, in conjunction with a remote processor that shares a portion of the processing. Additional mass storage devices (not shown) may also be connected to processor 102 through network interface 108.

An auxiliary I/O device interface (not shown) can be used in conjunction with computer system 100. The auxiliary I/O device interface can include general and customized interfaces that allow the processor 102 to send and, more typically, receive data from other devices such as microphones, touch-sensitive displays, transducer card readers, tape readers, voice or handwriting recognizers, biometrics readers, cameras, portable mass storage devices, and other computers.

In addition, embodiments of the disclosed technique further relate to computer storage products with a computer readable medium that contains program code for performing various computer-implemented operations. The computer-readable medium is any data storage device that can store data which can thereafter be read by a computer system. Examples of computer-readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. The computer-readable medium can also be distributed as a data signal embodied in a carrier wave over a network of coupled computer systems so that the computer-readable code is stored and executed in a distributed fashion. Examples of program code include both machine code, as produced, for example, by a compiler, or files containing higher level code that may be executed using an interpreter.

The computer system shown in FIG. 1A is but an example of a computer system suitable for use with the various embodiments disclosed herein. Other computer systems suitable for such use can include additional or fewer subsystems. In addition, bus 109 is illustrative of any interconnection scheme serving to link the subsystems. Other computer architectures having different configurations of subsystems can also be utilized.

Figure 1B:
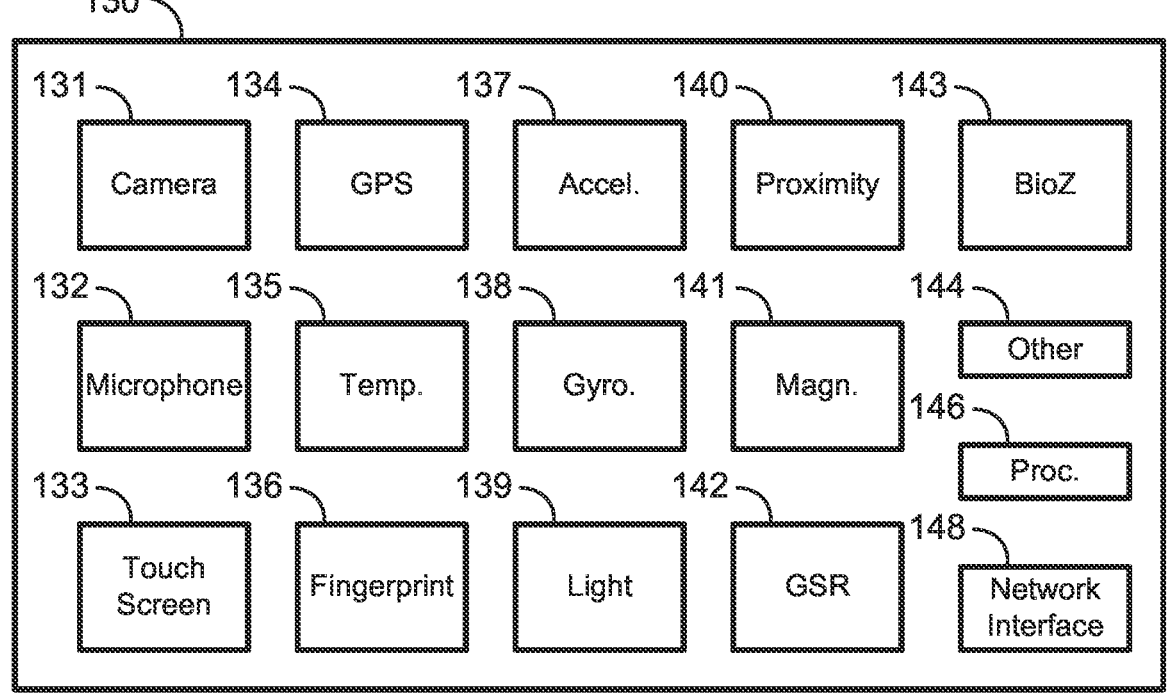
FIG. 1B is a block diagram of one embodiment of a client device usable in a system for detecting gestures for classi-fying movements.

FIG. 1B is a block diagram of one embodiment of client device 130 usable in a system for detecting movements and classifying the movements. Client device 130 may be a mobile or other computing device including one or more sensors. For example, client device 130 may include smart phones; wearables such as smart watches, or other wearable sensor devices as disclosed herein. In some embodiments, client device 130 is a wearable that is worn around the wrist and is substantially fixed with respect to the wrist when worn, such as a smart watch.

Client device 130 includes processor(s) 146 and memory 148 that are analogous to processor(s) 102 and memory 110/112, respectively. Client device 130 also incorporates a number of sensors 131 through 144. For example, client device 130 may include one or more of camera(s) 131 that may include an ultra-high definition camera, microphone(s) 132, touch screen(s) 133, global positioning satellite (GPS) system(s) 134, temperature sensor(s) 135, fingerprint identity sensor(s) 136, accelerometer(s) 137, gyroscope(s) 138, light sensor(s) 139, proximity sensor(s) 140, magnetometer(s) 141, galvanic skin response (GSR) sensor(s) 142, bioimpedance sensor(s) 143, and other sensors 144. Other sensors 144 might include infrared sensor(s), photoplethysmograph (PPG) sensor(s), electrocardiogram (ECG) sensor(s), moisture sensor(s), humidity sensor(s), digital barometric pressure sensor(s) and/or additional sensors not discussed herein.

Although sensors 131 through 144 are shown in FIG. 1B, client device 130 may include a subset of sensors 131-144, different sensor(s) and/or additional sensor(s). For example, client device 130 may include a range of sensors and/or devices not explicitly disclosed herein as new devices are released. In other embodiments, client device 130 may simply contain accelerometer 137 and gyroscope 138 as inertial sensors as well as processor 146, memory 148 and other components that may exist in a wearable such as a smart watch. For detecting gestures and classifying activities, accelerometer 137 and gyroscope 138 may be of particular use. Consequently, as used herein, an inertial measurement unit (IMU) includes at least one accelerometer 137 and at least one gyroscope 138. Although only one instance of the various sensors 131-144 are shown, in other embodiments, another number may be used.

Figure 2:
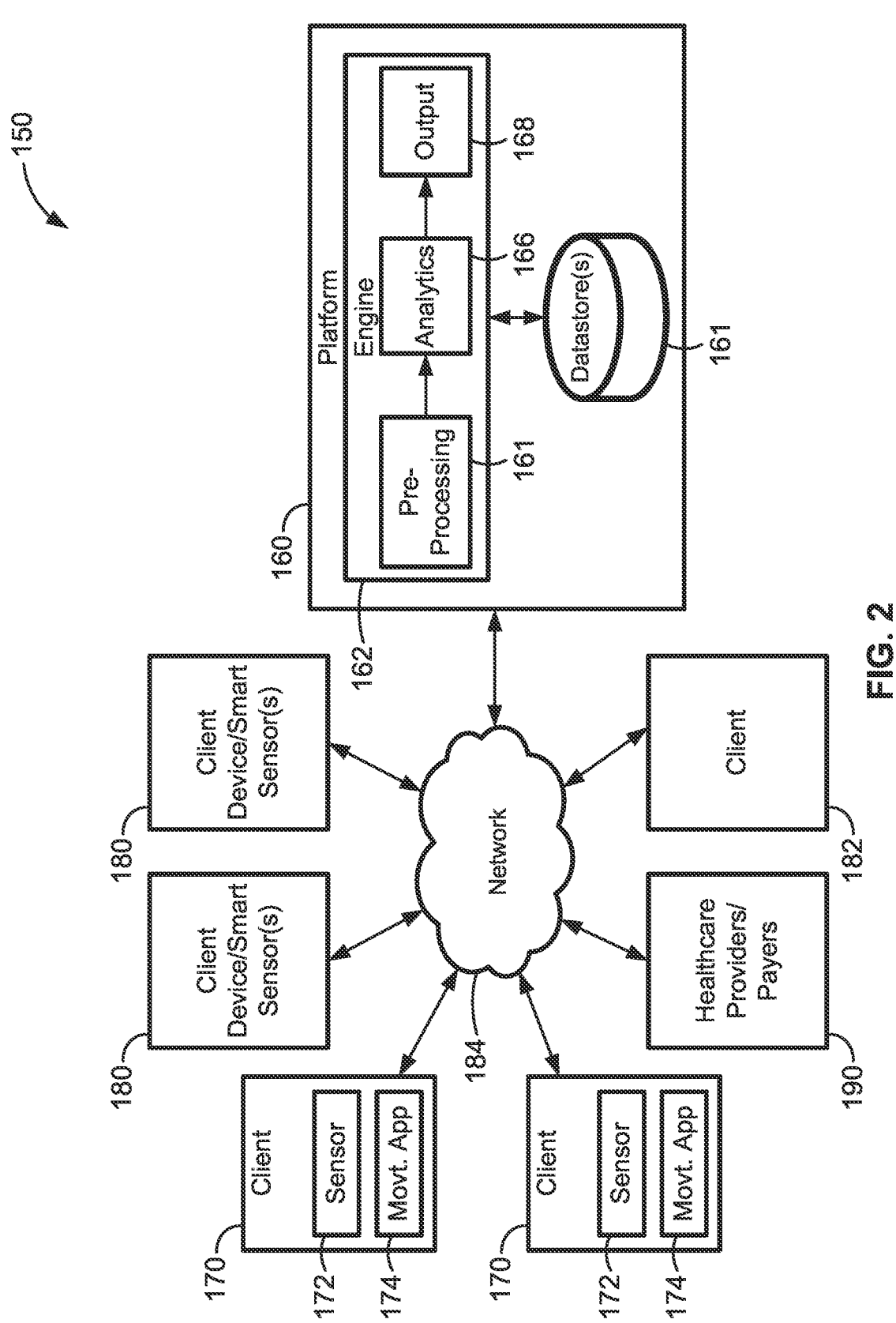
FIG. 2 is a block diagram of the architecture of one embodiment of a system for detecting gestures for classify-ing movements.

FIG. 2 is a block diagram of the architecture of one embodiment of system 150 for detecting and classifying movements. In particular, FIG. 2 illustrates one view of an embodiment of platform 160 and client devices 170, 180, and 182 coupled via network 184. Also shown are healthcare provider/payer systems (hereinafter "provider systems") 190. Network 184 includes one or more networks between devices 170, 180, 182, and 190 and phenotypic detection platform, such as the Internet, intranet networks, or local area networks. For simplicity, only certain portions of platform 160, client devices 170, 180 and 182 and provider system(s) 190 are shown in FIG. 2. Although only five client devices 170, 180, and 182 are shown as coupled to phenotypic detection platform 160, another number of clients typically utilize phenotypic detection platform 160. Phenotypic detection platform 160 may be implemented using computer system 100.

Client devices 170, 180, and 182 provide data to platform 160. Client devices 170 may be implemented using client 130. For example, client devices 170 may include mobile devices such as wearables described above. Client devices 170 include sensor(s) 172 analogous to those described above. Thus, client devices 170 include IMUs, processor(s) and memory. In addition, client devices 170 include movement application 174.

In some examples, movement application 174 receives sensor data captured/output by sensors 172, optionally performs processing on the sensor data and provides data to platform 160. Movement application 174 also receives communications from platform 160. For example, in some embodiments, movement detection takes place using engine 162 on platform 160. For example, engine 162 may preprocess sensor data received from clients in block 164, perform analytics to determine whether particular movements are being engaged in using analytics 166 and provide the appropriate output using component 168. Datastore 161 may store data for individual users of clients 170 as well as other information including trained classifiers. In other embodiments, some or all of the processing and analytics may be performed on clients 170. Further, although described in the context of the architecture of platform 160, in other embodiments, another architecture may be used.

The operation of accelerometers and gyroscopes is well known. In general, accelerometers such as accelerometer 137 output values indicating a force/acceleration in three dimensions. Thus, accelerometer 137 present in a wearable on a user's wrist (or in a smart phone held in a user's hand) provides a signal indicating the acceleration of a user's hand. A gyroscope, such as gyroscope 138, provides a measurement of rotation around one or more axes. Thus, gyroscope 138 provides an indicator of the orientation of a user's hand. Thus, an IMU provides data related to a user's body, for instance an acceleration of a user's hand, orientation of a user's hand, an acceleration/orientation of a user's body, as well as corresponding time stamps and duration of movements (e.g. the amount of time the user's hand is subject to the acceleration).

Further, as part of the method and system described herein, it may be desirable to know whether a smart watch or other wearable is being worn on the dominant or nondominant hand (or the left hand/right hand). This may affect weighting of training parameters and may be input as metadata into the system. The wearable user interface also provides easy access to the user to confirm labels through device prompts, in real-time, during behavior being trained for automatic classification.

Using the method and system described herein, statistics related to the detected/classified movements may be compiled. For example, the number of times per day, time of day, length of episode, etc. may be gathered each time the movement is detected or classified by the user. The user may see automatically tabulated frequency of a detected movement (e.g. smoking), time(s) of day, length(s) of episodes, etc. Similarly, the method and system may graphically present statistical results to the user via the smart watch or another device such as a smart phone, laptop, tablet or other computing device. Thus, the user can see automatically tabulated graphic visuals indicating how movements such as smoking change over time periods. The user can see automatically tabulated significance of their reduction or increase in the detected/classified behavior such as smoking. The reduction/increase may be provided with reference to their initial responses, such as responses to the Fagerström Test of Cigarette Dependence (FTCS).

To use movement application 174, the user may indicate which movements, such as smoking, are of interest. In response, movement application may prompt the user for more information. For example, the FTCS may be administered via movement application 174. Other information specific to the user may also be entered. Movement application 174 may also integrate of ECG or pulse rate measures during smoking episodes using other sensors 172.

To use the method and system described herein, multiple general phases may be present via movement application 174. In a first phase, the user may manually classify behaviors. For instance, the hand movements detected by the system may be labeled by the user as corresponding to specific behaviors, or ADLs, such as eating and/or smoking Additionally, allowing individual users to classify their behaviors may provide more rapid customization of movement application 172 to individual users.

Although one of ordinary skill in the art would understand how an accelerometer and gyroscope function and the signals provided, a brief discussion is provided for review.

Figure 3A:
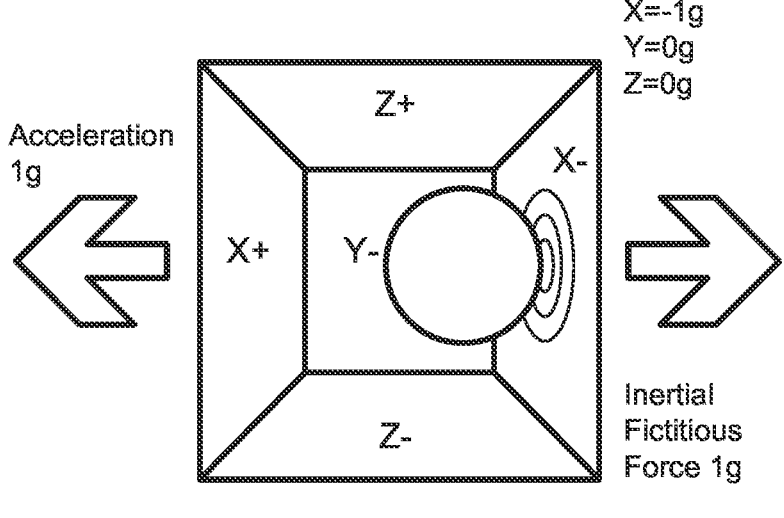
FIG. 3 is a diagram illustrating accelerometer operation.
Figure 3B:
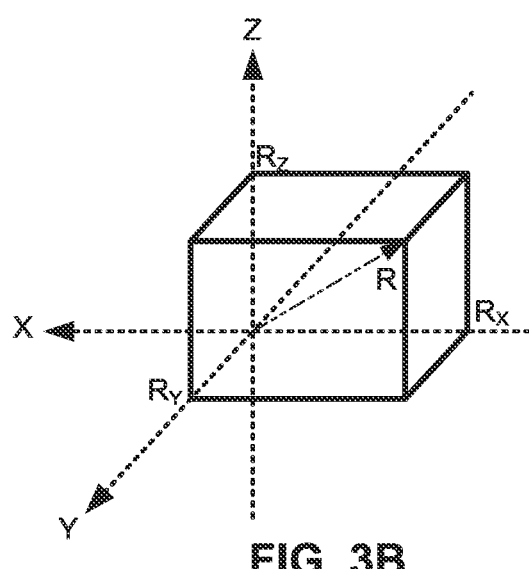

An accelerometer detects and outputs data related to a force that is directed in the opposite direction from the acceleration vector. This force is often called inertial force or fictitious force. FIG. 3 depicts an accelerometer and corresponding vectors used for discussion. The vector R is the force vector that the accelerometer is measuring (it could be the gravitation force, the inertial force from the examples above or a combination of both). For instance, Rx, Ry, Rz are the projections of the R vector on the X, Y and Z axes and may be governed by the relation: $R^2=Rx^2+Ry^2+Rz^2$. Accounting for the gravitation force is 1 g, and in units of "g": $1^2=(-SQRT(1/2))^2+0^2+(-SQRT(1/2))^2$. Assuming R is the unit vector, (R=1), Rx=−SQRT(1/2), Ry=0, Rz=−SQRT (1/2). The values Rx, Ry, Rz are linearly related to the values commercial accelerometers will output and that can be processed to classify movements.

Figure 4:
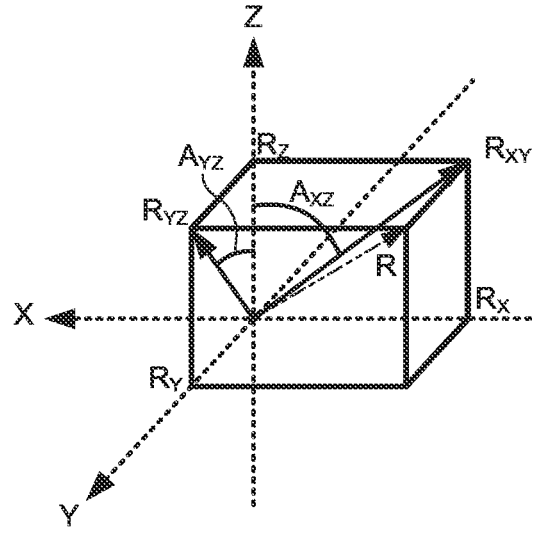
FIG. 4 is a diagram illustrating gyroscope operation.

FIG. 4 depicts operation of a gyroscope. Each gyroscope channel measures and outputs data relating to the rotation around one of the axes. For example, a 2-axes gyroscope will measure the rotation around the X and Y axes. Rxz− is the projection of the inertial force vector R on the XZ plane. Ryz− is the projection of the inertial force vector R on the YZ plane. From the right-angle triangle formed by Rxz and Rz, using Pythagorean theorem: $Rxz^2=Rx^2+Rz^2$ and $Ryz^2=Ry^2+Rz^2$. The gyroscope measures the rate of changes of the angles above, or a value that is linearly related to the rate of change of these angles. For example, the rotation angle around axis Y (Axz angle) at time t0, is defined as Axz0. This angle measured at a later time t1 is Axz1. The rate of change will be calculated as follows: RateAxz= (Axz1−Axz0)/(t1−t0). Expressing Axz in degrees, and time in seconds, then this value can be expressed in degrees/s.

Body Movement Monitoring Methods

Figure 5:
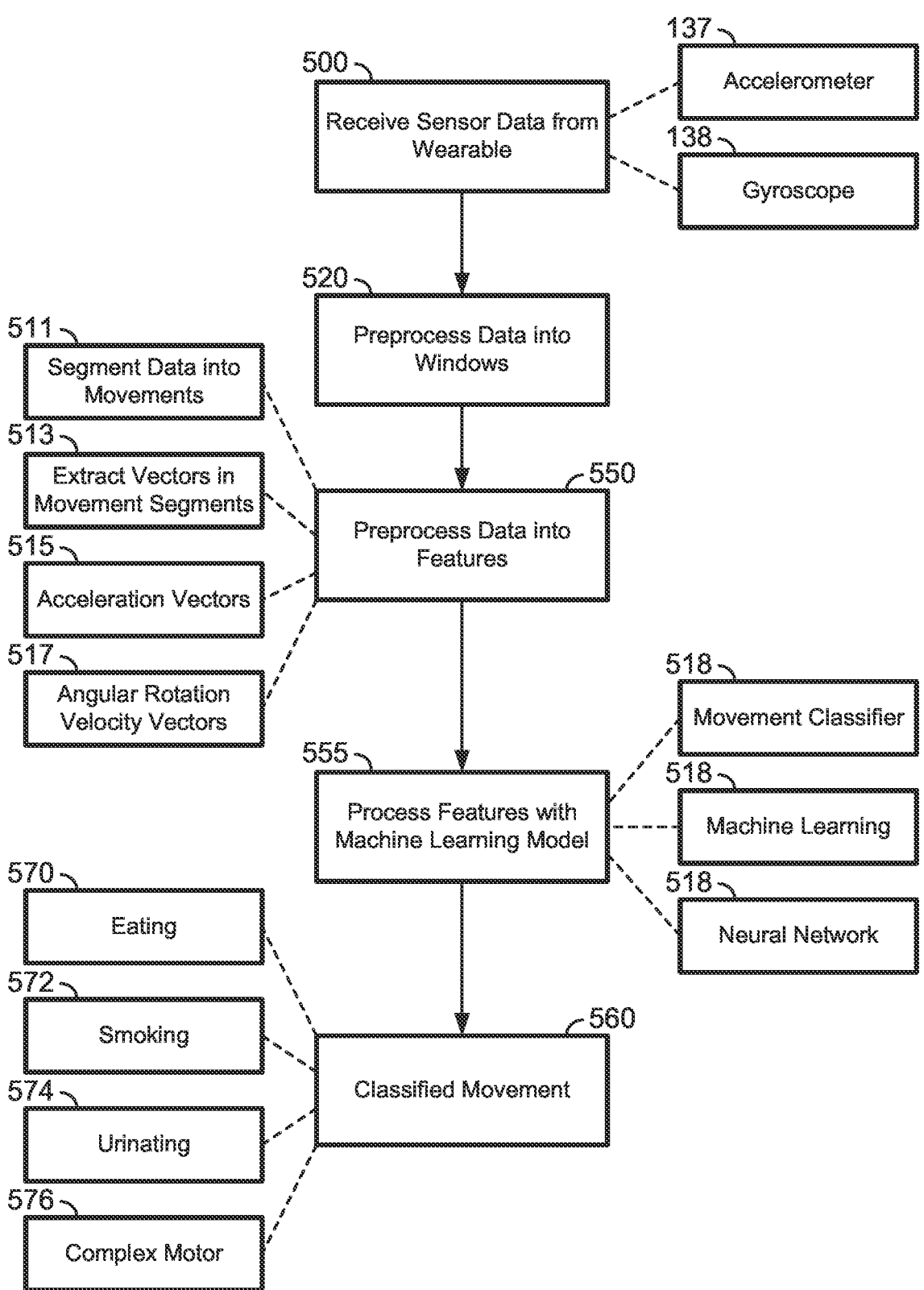
FIG. 5 is a flow chart illustrating an example method for processing sensor data to classify movements.

FIG. 5 is a flow chart illustrating an example process for receiving data from a wearable 500 and processing the data to output a movement classification 560. In some examples, the wearable 500 may include a smart watch, smart anklet, smart band around the waist or torso, a smart device (e.g. smart phone) inside in the pocket of a user or otherwise attached to a user's body, smart glasses or other smart devices coupled to a user's body.

Body Movement classifications 560 may include a variety of different movements, for instance: smoking 572, eating 570, urinating 574, complex motor movements 576, standing up, laying down, eating with hands, eating with fork and knife, eating with a spoon, drinking, lying down from sitting, sitting up in bed, standing up from sitting, walking, running, typing on a keyboard, writing, running, washing hands, brushing teeth, climbing stairs, descending stairs, and others as disclosed herein or would be contemplated by those of skill in the art.

In some examples, data collected will be from various sensors 130, including a gyroscope 139 and an accelerometer 137. In other examples, various other sensors 130 may be utilized as disclosed herein. The data may then be processed into windows 520 of various temporal length. For instance, the windows 520 may be 2, 3, 4, 5, 10, 20, 30, 40, 60 seconds, or 1, 2, 3, 4, or 5 minutes in duration. In some examples, the windows 520 may be sliding windows that are overlapping each other so that the disclosed technology may test windows for body movements. In some examples, where the sliding windows are overlapping, their starting point may be 0.01, 0.02, 1, 2, 10, 20, or 30 seconds, 1, 2, or 3 minutes apart (e.g. a 1 second offset).

For instance, in one example, the sliding windows may be 10 seconds long and offset by 1 second. This will enable the technology to look at a duration of sensor data that is long enough to capture a movement (e.g. eating) with a 1 second precision, so that it can accurately determine when the movement started and ended.

The sliding window(s) is particular useful so that temporal segments of sensor data may be tested that include an entire body movement—rather than a portion. Accordingly, shorter time segments that are closer together may be tested in some cases, or longer time segments that have little or no overlap may be tested—in which case most behaviors would not be partially cut off at the margins of the segments.

After the data is processed into windows, the sensor data may be preprocessed into features 550. This may include processing the data in each segment into movements 511 as described herein. This may also include extracting vectors in movement segments 513. For instance, acceleration vectors 515 and/or angular rotation velocity vectors 517 may be extracted from the sensor data or other data output by accelerometers 137 or gyroscopes 138. Various other vectors and features may be processed depending on the types of sensors and the movements that are being classified.

Next, the extracted features may be processed with a model, for instance a machine learning model 555. In some examples, the raw data or portions of the raw data after filtering may be input directly into a movement classifier 518. The movement classifier 518 may be various machine learning models, for instance a random forest model, decision tree, adaptive boosting, neural network, or support vector machine. In some examples, the machine learning model may output a discrete or binary result that indicates whether or not a temporal segment of sensor data contains data that indicates the user performed a particular body movement.

In one examples, there may be multiple rolling windows (e.g. 2, 3, 4, 5, 8, 10, 15, 20 etc.) applying a movement classifier at the same time. This will also allow comparing and averaging the results given to the different rolling windows and increasing the probability of accurately classifying a movement. For instance, a first rolling window may detect a movement, and the technology could record the time stamp of the starting point of the movement. The following rolling windows may confirm or invalidate this point (with a small degree of variation allowed). This enables the application to make sure that the starting point was correctly defined.

Once x % (e.g. 50%, 60%, 70%) of the rolling windows have confirmed the starting point, the technology could define this point as point A. An endpoint B may be defined in the same manner (once x % of rolling windows cannot identify a movement after a certain point in time, the point is defined as the endpoint B). While the rolling windows continue processing incoming data, in parallel, the technology may apply movement classifier(s) (one classifier or several depending on how many movements the technology is monitoring for) to the data between points A and B and output a label for that window (hereinafter "AB windows").

Additionally, if two (or more) consecutive "AB windows" are labelled as the same movement, the technology may determine that the movement actually lasted for as long as the time between the point A of the first of these "AB windows" and the point B of the last of these "AB windows". For example, if a user is eating lunch, but stops and rests before resuming their lunch, the technology may determine that the movement/behavior "eating lunch" is just one, by determining the lack of movement was only a pause in eating, which will allow for more accurate counting of individual meals.

As described herein, once a movement is classified, it may then be used for various additional applications as disclosed herein.

Figure 6:
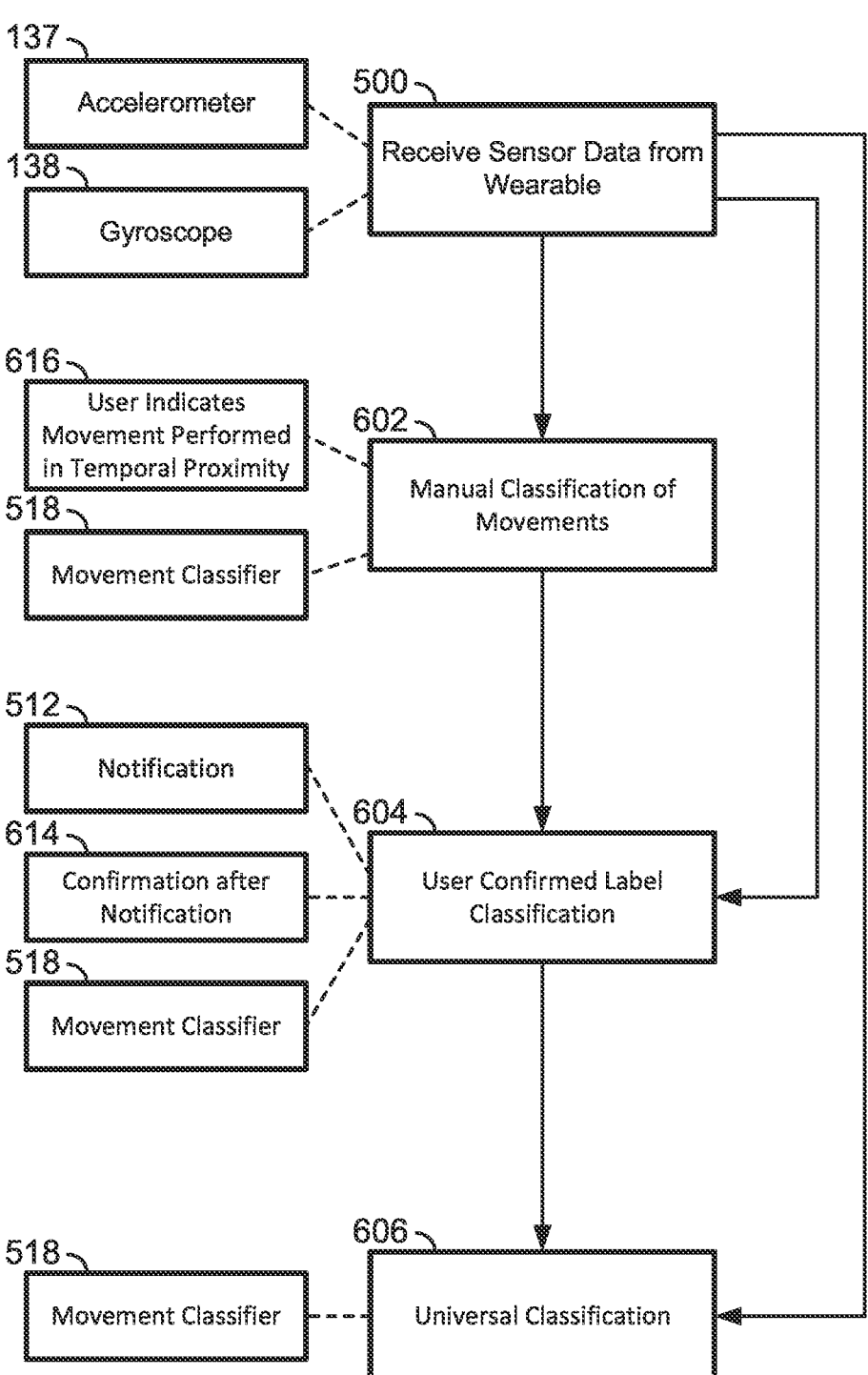
FIG. 6 is a flow chart illustrating example method for training movement classifiers.

FIG. 6 illustrates an example flow chart showing various methods to train the movement classifiers 518. For instance, the sensor data from a wearable 550 may be utilized in a manual classification step 602. For instance, to first classify a movement that has not been previously classified, a user may engage in the movement while wearing a client device 130 with sensors, for instance an accelerometer 137 and gyroscope 138.

Once the user engages in the movement, the user may click an interface component of the wearable or other client device 130 (e.g. touch screen 133). In other example, the user may audibly indicate a movement has been performed so that the movement of the user touching a touch screen does not interfere with the analysis by introducing noise into the sensor data. In that example, the disclosed technology may have an application or setting that is manual training, and the microphone 132 records audio data and listens for when a user indicates a movement is performed.

Once the technology receives an indication that a movement is performed within temporal proximity 616 (i.e., the movement has just been performed or will be performed), the system can process the data into windows 520 as described above with respect to FIG. 5 to identify a movement. This may include a time window before and after receiving the user indication, for instance, +/−5, 10, 15, 20, 30 40, 50, or 60 seconds, or +/−1, 2, 3, 4, or 5, minutes. In some examples, this may include identifying when the various vectors are above a threshold magnitude (to indicate a movement is being performed) and when they return to near zero or no movement. In this way, the cyclicality can be utilized to segment the data into discrete durations that include an entire movement/gesture/behavior/ADL. In other examples, the data might be analyzed for other indications a movement has started and stopped as disclosed herein to segment the data into portions that likely contain a movement.

Accordingly, once a movement has been manually entered into the system, a movement classifier 518 associated with that movement may be stored in memory 148. In future sessions, the user could manually classify the same movement several times, to update the movement classifier 518 associated with that particular movement in the memory 148.

Once there is a baseline or initial movement classifier 518 associated with a particular movement, the technology may include functions to allow the user to confirm the label classification 604 when the technology detects that the output sensors data indicates that movement is being performed. Accordingly, once a first movement classifier 518 for a first movement (e.g. eating) has been created, the technology may monitor the sensor data to detect the first movement using the first classifier.

Once a movement classifier 518 determines a particular movement (e.g. eating) likely has been performed, the application may send a notification 512 to the user on the device 130. The notification may request the user confirm 614 a certain movement was just performed or is being performed. Accordingly, a notification may be displayed on a touch screen 133 that allows the user to confirm a particular movement has been performed, or indicate which movement has been performed.

This allows the accuracy of the movement classifier 518 to be improved over time, as the movement classifier 518 will be updated every time the user confirms 514 a movement, and learn from the user's specificities. Additionally, because the user will not be manually classifying—but rather living their life normally and therefore performing movements naturally, the classification will have increased accuracy over when a user artificially performs a task to manually classify it.

In some examples, the user confirmed classifications 604 may be aggregated from a variety of users to output a universal classification 606 that will work with any user and will not require training or user confirmed confirmation 604. In that examples, the data, weights and other information from movement classifiers 518 saved on different client devices 130 may be aggregated to output a universal movement classifier 518 as disclosed further herein.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Example 1: Data Preprocessing

In some examples, data output from sensors may be preprocessed using various techniques, including those disclosed herein. For instance, the data output from sensors may first be preprocessed into features. In one example, the features may include the following features extracted from an accelerometer and gyroscope for a single user recorded session (e.g. manual classification session):

TABLE 1

| | | | | | | |
|---|---|---|---|---|---|---|
| Acceleration along axis x [g] | Acceleration along axis y [g] | Acceleration along axis z [g] | Angular velocity along axis x [deg/s] | Angular velocity along axis y [deg/s] | Angular velocity along axis z [deg/s] | Duration [s] |
| [1.016, 1.022, 1.024, 1.021, 1.0170000000000001, 1.015, . . .] | [0.8170000000000001, 0.82, 0.8190000000000001, 0.823, 0.818, . . .] | [0.599, 0.593, 0.595, 0.603, 0.604, 0.598, 0.601, 0.593, . . .] | [−13.11, −9.939, −5.4270000000000005, 2.6830000000000003, 6.768, 8.232000000000001, . . .] | [0.915, 0.305, −0.366, 0.976, 3.049, 5.0, 8.476, . . .] | [−1.402, −1.89, −1.22, 1.28, 2.012, 0.061, −2.927, . . .] | 29.98 |

Example Preprocessed Features

As illustrated in Table 1, the data may be preprocessed into the following features: acceleration along the x, y, and z axis; angular velocity along the x, y, and z axis; and duration. In some examples, the sensors may be sampled at 30, 40, 50, 60 Hz or other suitable frequency. Accordingly, each feature may include a reading at a particular time point (e.g. ever 0.01 or 0.02 seconds). The duration relates to duration of the entire session, in this case. For manual classification, the session data in Table 1 would have a specific label based on the user input relating to a particular movement the user performed. For instance, the ground truth label for this data may be "eating" if the user was manually classifying an eating movement.

Accordingly, this data set may be preprocessed in various other forms, including to transform the matrix into a two dimensional matrix, that includes the features at every sampled time for the entire session. Then, the features may be input into a movement classifier as disclosed herein for training or classification purposes.

Example 2: Phased Classification—Smoking and Eating

Following is one example of phased classification of body movements according to the disclosed systems and methods. Phase I (Manual Classification-Individual)

A small pilot cohort of users wearing IMU-based sensors (accelerometer and gyroscope) (e.g. in smart watches) may be utilized to manually classify movements associated with smoking. As described herein, the users may perform smoking movements while the sensors record the data which is then preprocessed into features. The disclosed technology would then label the data with a smoking output label, as the ground truth movement label.

For instance, accelerometer (tri-axial accelerometer provides magnitude of acceleration in x, y, z directions in units "g": 1 g=9.81 m/s²) and gyroscope data (gyroscope provides angular rotation velocities in units "radians per second") is collected across temporal periods (milliseconds). These sensors will output data which may then be stored in a database/ memory in a table.

Accordingly, in this example because there is no existing data associated with smoking in the system or any trained classifier, the users must manually classify the smoking behavior by indicating on an interface of a wearable, for instance by tapping a watch face) that they will perform/ have performed the smoking movement. Sensors data will be sampled at 50 Hz and recorded at a time "t" of −2/+2 minutes around the smoking episode (i.e. point at which the user taps the smart watch). In some examples, the data will be preprocessed into vectors as described in Example 1 above.

Preprocessing Based on Cyclicality

In other examples, additional preprocessing, and/or segmenting of the data may be performed based on the cyclicality of certain movements like smoking. In that examples, preprocessing may include the output of cyclicality related features. For instance, a smoking episode consists of the entire time indicated above and typically involves multiple cycles of hand motions of waist (or other starting location)-to-mouth and mouth-to-waist (or other ending location) gestures ("puffs"). Thus, each episode includes multiple cycles.

Each smoking cycle includes several smoking specific mechanical/kinetic motion unique features, which may be derived from the combination of the accelerometer (dv/dt) and gyroscope (dθ/dt) data. For instance, the x axis may be defined as the forward/backward looking direction from the perspective of the user, the y axis as the lateral directions (right/left), and the z axis as the up/down directions. The inflection points may be considered to be the middle of the gesture/movement—for smoking, it would be the time that the hand pauses at the mouth for the user to take a puff from the cigarette (which is considered synonymous with an e-cigarette, cigar or other smoking device).

Accordingly, the data may be preprocessed to identify cycles or starting, inflection, and/or end points of cycles. For instance, for each of the several cycles within a single classified behavior such as smoking may be somewhat approximated as:

hand, at waist: As the hand rests stationary at waist level, only gravitational pull affects the accelerometer and angular velocity are approximately zero along all three axes.

$$\frac{dv_x}{dt} \approx 0, \frac{dv_y}{dt} \approx 0, \frac{dv_z}{dt} \approx g$$

$$\frac{d\theta_x}{dt} \approx 0, \frac{d\theta_y}{dt} \approx 0, \frac{d\theta_z}{dt} \approx 0$$

hand, back to mouth: As the hand is raised to the mouth, it rotates along the lateral axis, accelerating upwards and in the backwards direction towards the mouth.

$$\frac{dv_x}{dt} < 0, \frac{dv_y}{dt} \approx 0, \frac{dv_z}{dt} > g$$

$$\frac{d\theta_x}{dt} \approx 0, \frac{d\theta_y}{dt} < 0, \frac{d\theta_z}{dt} \approx 0$$

hand at mouth for smoke inhalation: During inhalation, the hand is momentarily (2-3 seconds) stationary again.

$$\frac{dv_x}{dt} \approx 0, \ \frac{dv_y}{dt} \approx 0, \ \frac{dv_z}{dt} \approx \frac{d\theta_x}{dt} \approx 0,$$

$$\frac{d\theta_y}{dt} \approx 0, \ \frac{d\theta_z}{dt} \approx 0$$

hand moved down to waist again: As the hand drops, it rotates along the lateral axis, accelerating downwards and in the forward direction. In some embodiments, therefore, the range of motion for smoking may be at or around the finger-to-shoulder length for a particular user. For eating, the range of motion for the user may be on the order of half this distance. The acceleration detected may be:

$$\frac{dv_x}{dt} > 0, \ \frac{dv_y}{dt} \approx 0, \ \frac{dv_z}{dt} < g$$

$$\frac{d\theta_x}{dt} \approx 0, \ \frac{d\theta_y}{dt} > 0, \ \frac{d\theta_z}{dt} \approx 0$$

Cycles repeat at least once and potentially multiple times. Accordingly, the data points that correlate to these points of the cycle may be labeled according, and used to segment the data into cycles and/or otherwise output cycle related features. In some examples, classifiers may be developed/trained to only identify classifications of particular portions of a smoking movement, for instance putting the user's hand to their face.

In some examples, cyclicality may generally be determined through analysis of autocorrelation measures on the accelerometer data. For example:

$$P = \arg \max_{\tau} \int f(t)f(t - \tau)dt,$$

where $\tau > 0$ where f(t) is assumed to be a signal corresponding to one cycle described in (a) through (d) described above and $\tau$ is the time taken for one cycle. It is expected that similar hand motions will produce cyclical readings along the x, y, z vectors, which will show a peak corresponding to the period of motion.

By segmenting data along these cycles, vector values can be overlaid with one another in order to extract mean vector values, along with degrees of variance along all three coordinates throughout the smoking gesture. These values allow "typical" spatial-temporal patterns of motion common among the cohort to be derived, as well as identify user-specific gestures for a more personalized detection procedure.

Fine-tuning and noise reduction may be made by only extracting smoking behavior data from the total temporal period under analysis. In some examples, this behavior may be segmented out based on correlation functions described above.

Accordingly, in some examples, kinetic vector values for dv/dt and dθ/dt established from many phase repeats of smoking cycles and many classified episodes are collected for the user. A coefficient of variance may be used, because that is a fraction that may be more readily compared. For example, a c.o.v=ratio of standard deviation to the mean, i.e. "relative variance". cov=sd/mean×100 may be used.

By segmenting the sensor data along these cycles (normalizing cycles by appropriate spatial and temporal scaling), vector values may be overlaid with one another in order to extract mean vector values, along with degrees of variance along all three coordinates throughout the smoking gesture. These values will allow "typical" spatial-temporal patterns of motion common among the cohort to be derived. In addition, user specific gestures may be identified for a more personalized detection procedure. Upon aggregating data from at least 10, 50, 75, 100, 125, 150, or other number of smoking sessions, user smoking cycles may be segmented out, and variances in vector values throughout the cycle calculated. In some examples, using these variances, 95% confidence intervals that this band over the 90% of the cycle will be positively identified as smoking movements.

In other examples, as explained above, the features that do not relate to cyclicality will be input into a movement classifier. Accordingly, the systems and methods may be utilized to manually train and/or generate a movement classifier on a new movement, such as smoking.

Phase IIA (User Confirmed Label Classification-Individual)

After an initial classifier is trained or developed, the system and methods may utilize user confirmed label classification to improve or train new movement classifiers that are specific to a particular user. In some embodiments, machine learning, in particular a recurrent (LSTM) neural network, may be used. This classification may be performed based on various combinations of features described above, with the training on appropriately labeled data derived from the user inputs as described above.

The disclosed system and methods may be utilized to classify body movements from sensor data. In some examples, the sensor data may be continually monitored to identify potential movements by applying a trained movement classifier to windows of output sensor data. Accordingly, once the technology identifies a potential positive classification of a particular movement, for instance smoking, the systems and methods may provide to the user a notification requesting confirmation that the user was smoking. For example, a label-confirmation such as "Are you smoking?" Click "Yes" or "No" may be provided in a notification. If the user clicks "Yes" on an interface, the trained movement classifier may be updated with the new data. However, if the user clicks "No," the classifier would not be updated. By providing additional labeled data, through user feedback, the method and system may increase its accuracy of classifying smoking movements for a particular user.

For a particular user, these prompts may continue until an established accuracy threshold is reached. For example, the threshold may be 90% of the last 100 label notifications were "Yes" and confirmed by the user). As a result, false-positives should be reduced over time and the systems and methods can track the accuracy based on whether the user clicks "Yes" or "No" and therefore may continue to request confirmation until a sufficient Yes/No ratio is reached over time.

After sufficient accuracy is reached, notifications requesting user confirmation of labels may stop and the individualized classification algorithm for a particular user saved in a memory for future use. Therefore, the systems and methods, over repeated smoking episodes, generates a movement classifier, (in one example, this would effectively be an optimized set of acceleration and angular velocity vector values as a function of time) that is specific and personalized to the individual user. Additionally, this trained movement classifier may be utilized for new users, to bypass the manual classification portion and/or lower the amount of user labeled confirmations are required to personalize a movement classifier to a particular user.

In some embodiments, even after the user confirmation phase is terminated, the user may be sporadically prompted by to confirm a detection of smoking (in this example). For instance, every 50-100 detections, spot checking/calibration may be performed. In some embodiments, this is accomplished by the confirmation request described above. In addition to ensuring continued operation, such a feature provides a reminder to the user that the behavior (e.g. smoking) is being tracked. This may provide comfort to user that they are still improving it and keeping detection of the behavior accurate. In some embodiments, Phase IIa turns on again if the variance between classified vectors starts to widen beyond 1.5 SD.

Phase IIB (Universal Classification)

In some examples, by aggregating the movement classifiers personalized to particular users, a universal classifier may be developed. This may include training a universal classifier on training data aggregated from many different users (including classifiers trained using only non-cyclicality related features) in Phase IIb.

For instance, in one example, analysis of data by ANOVA packages provides variation, standard deviation and coefficient of variance to the mean baseline values of a population. Population-wide commonalities may be determined and implemented in various processing or preprocessing steps. Thus, a new adopter of the app (for example, after the $101^{st}$ User) will not have to manually classify the smoking behavior or may have a shorter (fewer episodes) classification session. With baseline values in place, smoking is automatically detected as above if the smoking cycle falls within the population-wide 95% confidence interval for 90% of the cycle. For durations within this range less than 90%, prompts for user labels will be requested in order to train the user-specific algorithm.

Wrist-wear instruments can be prone to systematic errors due to random hand movements. These errors may be mitigated through analysis of periodic motions during smoking. Since a typical smoking episode consists of multiple common gestures with each pattern of raising the cigarette to the mouth, inhalation (0 vector value pause), and removal of the cigarette, variations in this range of motion may be diminished when multiple periodic patterns are analyzed in aggregate. Variation in user smoking and eating habits can affect the typical "cyclical pattern" and make it difficult to judge common vector baseline values for a population. Manual classification in Phase I described above may be used to detect both user-specific features, as well as population wide characteristics. Some false positives may be expected if the motion is non-cyclic. For example, wiping nose with tissue, drinking, employ similar mechanical motions. It is expected, however that although these motions may appear similar over a single cycle. The degree of recurrence and temporal period of these gestures should distinguish themselves from smoking motions over a longer time frame (minutes). Thus, in some embodiments, a minimum threshold of cycle repeats within a particular time may be required for a detection of smoking.

Sensitivity and specificity of detection can deteriorate in real-world settings. Thus, use of the user data (and development of a database including data for multiple users) as described above in Phase I % may improve performance. Further adaptive algorithms may be developed.

In addition, a user may move while smoking. For example, there may be a distinct difference in smoking patterns when comparing smoking while sitting/standing versus walking. In the case of walking, existing algorithms that have been extensively developed detect walking mechanics (which are cyclic). These cyclic motions may be filtered to derive underlying hand motions which may be indicative of smoking while walking. If user smart phone accelerometer data are also available, these can also be used to measure vector values associated with walking. The signals corresponding to these motions can then be subtracted off from the watch signal to isolate signals originating from hand motions due to smoking.

In Phase I and Phase IIa above, in addition to labeling smoking/confirming smoking, the user may be prompted to label/confirm data for "sitting/standing smoking" versus "walking smoking" In this case, the process proceeds as described herein. However, the requests for confirmation/user input may be halted once the user has confirmed detection achieves a 90% accuracy rate over at least 100 smoking sessions for each of standing/sitting and walking. In other embodiments a 90% accuracy in 100 total smoking sessions may be sufficient.

The data/vectors derived from the accelerometer(s) and gyroscope(s) can be determined to be measured as kinetics relative to earth vs relative to the self. In some embodiments, this may distinction may be determined in conjunction with a smart phone. The smart phone may provide signals for vector values relative to earth, while a smart watch provides vector values relative to earth+self. The smart phone vector values may be subtracted from the watch vector values to obtain net-net kinetic values relative to self. Additionally, this feature is incorporated into most existing IMU sensors, and therefore in other embodiments, this may be directly calculated by the IMU.

Smoking while standing and smoking while sitting may be detected in the same manner. Standing/sitting has no kinetic change relative to earth, so differences in the user's position should not change the discussion above. If a user is walking or moving in a normal way, which tends to be walking, this can be treated as described above.

Eating

The above has been described with respect to detection of smoking. Data from an IMU may be obtained from a patient population who are instructed to eat and label the data. Thus, Phase I may be performed for eating. This may provide a ground truth baseline (e.g. an assumed set of vectors that appear to be the motion of a hand when eating, or a trained movement classifier). Further, these motions may be correlated with additional context such as time of day, duration of eating/activity etc. to further corroborate what would be the baseline assumption of eating classification. Phase IIa and IIb may proceed iteratively to obtain sufficient data for detecting gestures corresponding to eating.

The disclosed methods and systems may provide thresholds, not relative to what the global "normal" is threshold, but to think about it relative to the user/self—temporally. Thus, time dimension may be inserted. Analytics can then also be based on individual changes longitudinal in time, rather than individual vs. a global threshold at a static moment in time. In such a longitudinal case, we can consider a "threshold" to be 1, 1.5, 2, etc. standard deviations from an individuals established retrospective baseline/average. The standard deviation values may also start with some ground truth assumptions and then be optimized more precisely via neural nets based on particular co-variables and depending on the application/disease.

For example, for eating, a dataset may be acquired. The dataset contains data from a particular number of users (also referred to as subjects or participants), each identified with a universally unique identifier (UUID). The category of "eating" may be included as one of the labels a user can employ in labeling/classifying activities. So, "eating" vs. "not eating" dataset may be derived from these labels.

Phase IIa may also proceed as described above for smoking. A universal baseline set of values and/or movement classifier may be able to be established from this dataset (e.g. Phase IIb may also be employed). The procedure above may be iterated and optimized with new human subjects in Phase IIb. A universal baseline and/or movement classifier can then be optimized user by user (label confirmed by user on smart watch to train the model to optimize ideal values—for that user) and in the process optimize a more universal method and system.

Iterating and repeating the method for each new user which will lead to a more accurate universal method and a more custom method for that individual user. Further, access to the underlying raw accelerometer and gyroscope data (pre-analysis) may be sufficient to analyze to provide some initial quantitative thresholds.

For smoking, if the smart watch including the movement application 174 is on the dominant smoking hand, a set of data/vectors that indicate acceleration to the face/mouth, pauses in space for a second or two, and then quickly accelerated downward/away from the mouth may be obtained. As a result, monitoring smoking frequency, smoking cessation programs with insurers/doctors, pharma trials to measure the smoking cessation efficacy of for an improved Chantix drug, and other applications may be improved.

The method and system may be extended to other movements as disclosed herein. Monitoring movements may be used to make inferences regarding changes related to basic and complex motor hand tasks that are parts of higher order movements such as ADLs. For example, this may be used to detect motor apraxia as an early indicator of neurodegenerative diseases/disorders.

Example 3: Improved Accuracy with User Confirmed Movements

FIG. 7 illustrates a line graph showing the improvement of the accuracy of a movement classifier 518 each time a user confirms a movement was performed. Accordingly, after only ten sessions per type of movement, the movement classifier improved to 93.75% accuracy for a particular user. Accordingly, the data illustrates the importance of user labeled confirmations to customize a movement classifier 518 for a particular individual. In this example, a user generated a testing dataset comprised of five movement sessions per type of movement.

The results suggest that with about five days of a user confirming movements, the accuracy could reach nearly 93.75% accuracy. Accordingly, this requires minimal investment and training for a particular user, as customizing the data had such a large impact on the accuracy.

Figure 8A:
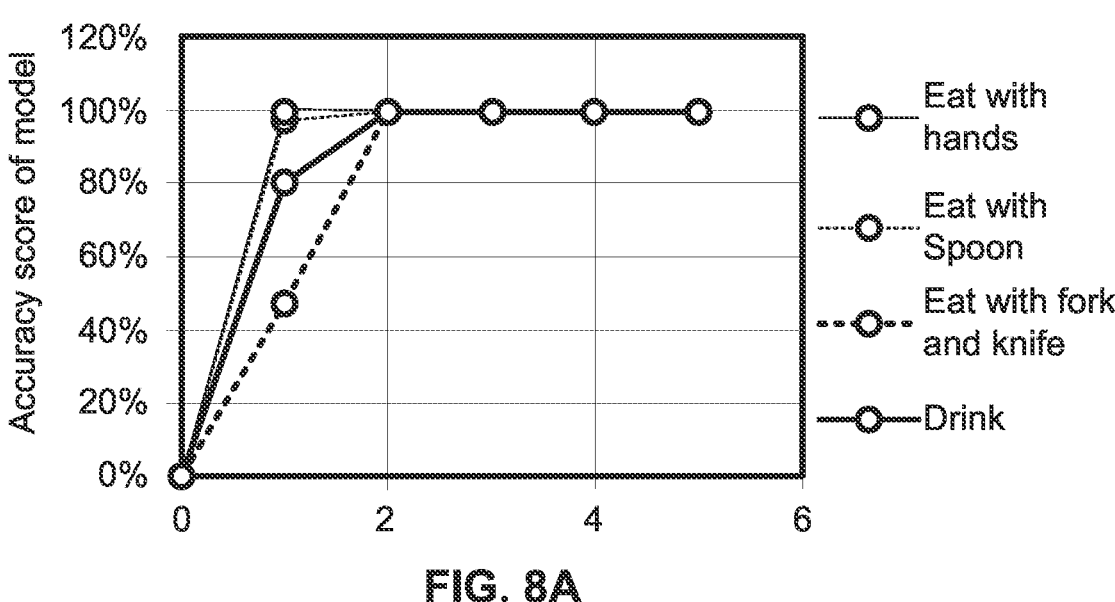
FIGS. 8A-8D are line graphs illustrating the accuracy improvement of various classifiers trained with user labeled sessions.
Figure 8B:
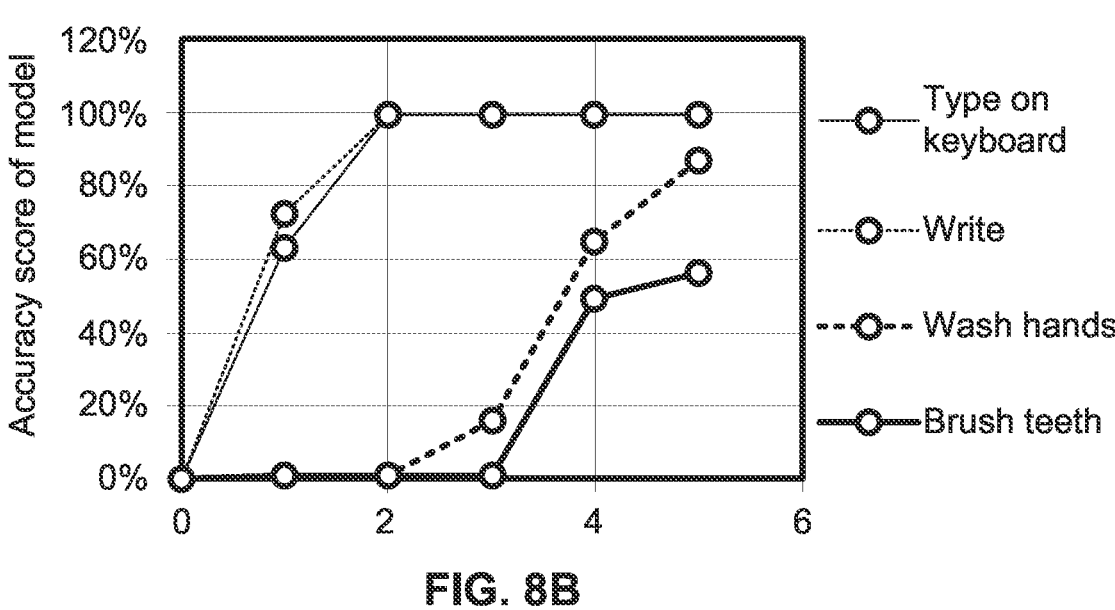
Figure 8C:
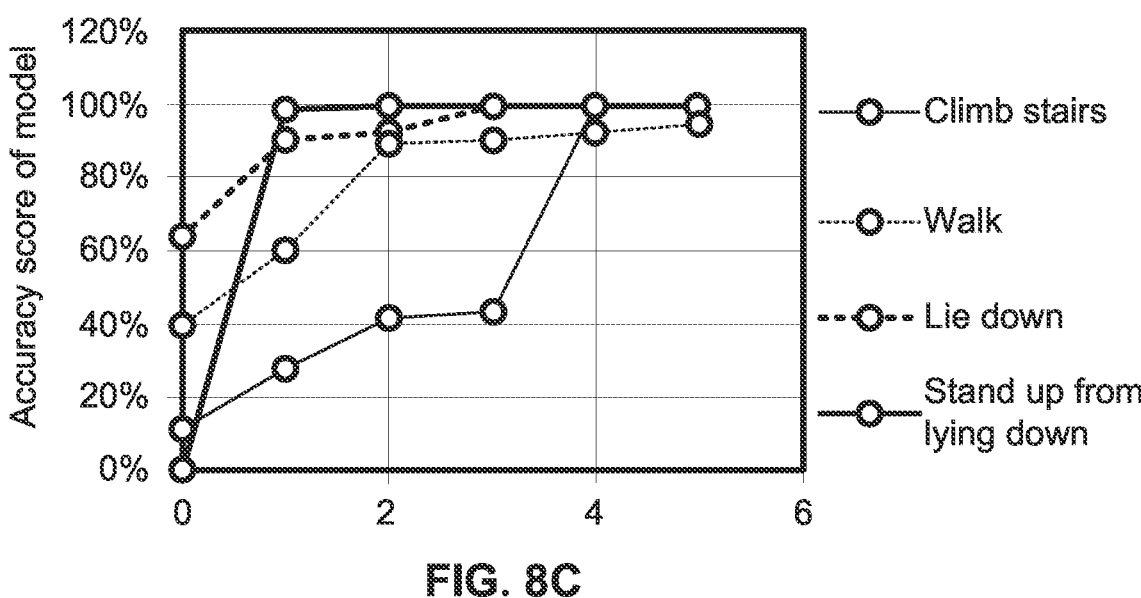
Figure 8D:
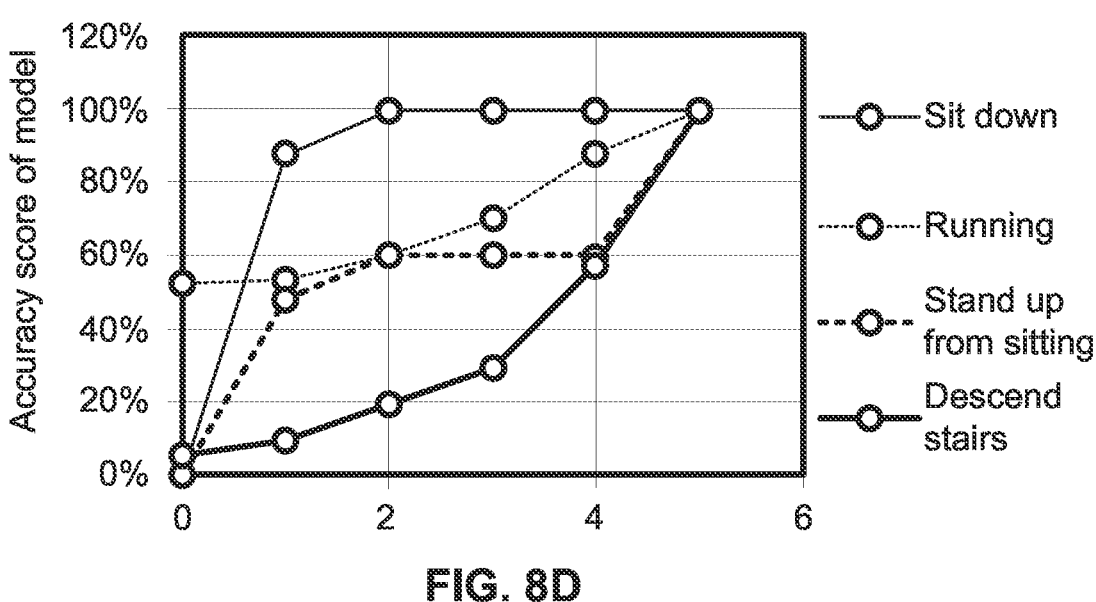

FIGS. 8A-8D illustrate classifiers relating to specific movements and their improvement in accuracy after five training sessions per type of movement. FIG. 8A involves movements that include cyclic hand movements. FIG. 8B involves movements that include only non-cyclic hand movements. FIGS. 8C and 8D involves whole body movements. While the movement classifiers 518 related to cyclic hand movements performed the best, one can see that all of the different classifiers improved to greater than 90% accuracy after only five training sessions per type of movement.

This is advantageous, because classification of movements from prior technology is relatively inaccurate, as most prior innovations use only universal classifiers. As each individual's movements, anatomy, and muscles are different, the peculiar way they move can be captured by requiring user confirmed labelling of the movements to improve the classifiers.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Selected Embodiments

Although the above description and the attached claims disclose a number of embodiments of the present invention, other alternative aspects of the invention are disclosed in the following further embodiments.

Embodiment 1. A method comprising:
    receiving a set of sensor data comprising data output from an accelerometer and a gyroscope;
    preprocessing the set of sensor data to output a set of features;
    processing the set of features with a movement classifier to output a movement classification;
    providing a notification to a user to confirm the movement classification on an interface;
    receiving a set of user input confirming the movement classification; and
    updating the movement classifier to output an updated movement classifier based on the set of user input.

Embodiment 2. The method of embodiment 1, wherein the notification is a pop-up message on a touch screen interface.

Embodiment 3. The method of embodiment 2, wherein the user input is an interaction with the touch screen interface comprising a confirmed label of the movement.

Embodiment 4. The method of embodiment 1, where updating the movement classifier comprises training the classifier with the set of sensor data using the confirmed label of the movement.

Embodiment 5. The method of embodiment 1, wherein the set of features comprises: acceleration along an x axis, acceleration along a y axis, acceleration along a z axis, angular velocity along axis x, angular velocity along the y axis, and angular velocity along the z axis, and duration.

Embodiment 6. The method of embodiment 1, wherein the movement classification comprises: eating, eating with hands, eating with fork and knife, eating with spoon, drinking, lying down, sitting down, standing up, walking, running, typing on keyboard, writing, washing hands, brushing teeth, climbing stairs, and descending stairs.

Embodiment 7. The method of embodiment 1, wherein preprocessing the set of sensor data further comprises segmenting the data into a set of time windows.

Embodiment 8. The method of embodiment 1, wherein the time windows are overlapping.

Embodiment 9. The method of embodiment 1, wherein the set of features comprise at least one feature related to cyclicality.

Embodiment 10. A method of manual classification comprising:

receiving a set of sensor data comprising data output from an accelerometer and a gyroscope related to a movement performed by a user;

preprocessing the set of sensor data to output a set of features;

receiving an input from the user comprising a manual label for the movement with a time stamp;

training a movement classifier with a portion of the set of features in a threshold temporal proximity to the time stamp using the manual label;

storing the movement classifier in a memory; and processing a second set of sensor data output from an accelerometer and a gyroscope to output a second set of features; and processing the second set of features with a movement classifier to output a movement classification.

Embodiment 11. The method of embodiment 10, wherein the threshold temporal proximity is +/−two minutes.

Embodiment 12. A system, the system comprising:

a wearable device;

at least one movement sensor incorporated into the wearable device;

a memory containing machine readable medium comprising machine executable code having stored thereon instructions;

a control system coupled to the memory comprising one or more processors, the control system configured to execute the machine executable code to cause the control system to:

receive a set of sensor data from the movement sensor;

preprocess the set of sensor data to output a set of features;

process the set of features with a movement classifier to output a movement classification;

provide a notification to a user to confirm the movement classification on an interface;

receive a set of user input confirming the movement classification; and update the movement classifier to output an updated movement classifier based on the set of user input.

Embodiment 13. The system of embodiment 12, wherein the control system is further configured to:

receive a second set of sensor data from the movement sensor;

preprocess the second set of sensor data to output a second set of features; and process the second set of features with the updated movement classifier to output a movement classification.

Embodiment 14. The system of embodiment 12, wherein the movement sensor comprises an accelerometer and a gyroscope.

Embodiment 15. The system of embodiment 12, wherein the movement sensor comprises an accelerometer, gyroscope, and magnetometer.

Embodiment 16. The system of embodiment 12, wherein the wearable device is a smart watch, smart anklet, or smart band.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A method comprising:

receiving a set of sensor data comprising data output from an accelerometer and a gyroscope;

preprocessing the set of sensor data to output a set of features;

processing the set of features with a cyclical individualized movement classifier for a user to output a movement classification, wherein the movement classification comprises one or more of eating, eating with hands, eating with fork and knife, eating with spoon, drinking, lying down, cyclical exercise motions, washing hands, brushing teeth, toilet usage, repeated contact with different anatomic regions, or other cyclical motions that can quantify the time, frequency, and duration of activities of daily living;

providing a notification to the user to confirm the movement classification on an interface;

receiving user input confirming the movement classification;

in response to the user input, generating a plurality of rolling, overlapping time windows over the sensor data within a preset interval before and after a time of the user input, and concurrently processing the plurality of rolling, overlapping time windows in parallel with the cyclical individualized movement classifier;

determining, based at least in part on agreement of at least a threshold percentage of the plurality of rolling, overlapping time windows, a start time A and an end time B of the confirmed movement:

defining AB windows as those rolling, overlapping time windows of the plurality of rolling, overlapping time windows whose ranges fall between the start time A and the end time B;

computing cycle features from the AB windows;

updating, on a device comprising the cyclical individualized movement classifier, the cyclical individualized movement classifier for the user by training the cyclical individualized movement classifier using the confirmed movement classification and the cycle features from the AB windows, to generate an updated cyclical individualized movement classifier for the user;

compiling statistics related to the movement classification;

establishing a baseline of movements based on the statistics, wherein the baseline is specific to the user; and predicting risks of health conditions based on changes of the movements relative to the established baseline of the user.

2. The method of claim 1, wherein the notification is a pop-up message on a touch screen interface.

3. The method of claim 2, wherein the user input is an interaction with the touch screen interface comprising a confirmed label of the movement classification.

4. The method of claim 1, wherein the set of features comprises: acceleration along an x axis, acceleration along a y axis, acceleration along a z axis, angular velocity along axis x, angular velocity along the y axis, and angular velocity along the z axis, and duration.

5. The method of claim 1, wherein the preprocessing the set of sensor data further comprises segmenting the data into a set of overlapping time windows.

6. The method of claim 1, wherein the set of features comprise at least one feature related to cyclicality.

7. The method of claim 1, wherein each of the plurality of rolling, overlapping time windows has a duration between 1 and 3 seconds and an overlap between 50 percent and 75 percent.

8. The method of claim 1, wherein the threshold percentage is 50 percent, 60 percent, or 70 percent.

9. The method of claim 1, wherein the preset interval spans two minutes before and two minutes after the time of the user input.

10. The method of claim 1, wherein updating the cyclical individualized movement classifier comprises storing updated parameters in a memory of the wearable device.

11. A system, the system comprising:

a wearable device;

at least one movement sensor incorporated into the wearable device;

a memory containing machine readable medium comprising machine executable code having stored thereon instructions;

a control system coupled to the memory comprising one or more processors, the control system configured to execute the machine executable code to cause the control system to:

receive a set of sensor data from the at least one movement sensor;

preprocess the set of sensor data to output a set of features;

process the set of features with a cyclical individualized movement classifier for a user to output a movement classification, wherein the movement classification comprises one or more of eating, eating with hands, eating with fork and knife, eating with spoon, drinking, lying down, cyclical exercise motions, washing hands, brushing teeth, toilet usage, repeated contact with different anatomic regions, or other cyclical motions that can quantify the time, frequency, and duration of activities of daily living;

provide a notification to the user to confirm the movement classification on an interface;

receive user input confirming the movement classification;

in response to the user input, generate a plurality of rolling, overlapping time windows over the sensor data within a preset interval before and after a time of the user input, and concurrently process the plurality of rolling, overlapping time windows in parallel with the cyclical individualized movement classifier;

determine, based at least in part on agreement of at least a threshold percentage of the plurality of rolling, overlapping time windows, a start time A and an end time B of the confirmed movement;

define AB windows as those rolling, overlapping time windows of the plurality of rolling, overlapping time windows whose ranges fall between the start time A and the end time B;

compute cycle features from the AB windows;

update, on the wearable device or a paired device, the cyclical individualized movement classifier for the user by training the cyclical individualized movement classifier using the confirmed movement classification and the cycle features from the AB windows, to generate an updated cyclical individualized movement classifier for the user;

compile statistics related to the movement classification;

establish a baseline of movements based on the statistics, wherein the baseline is specific to the user; and predict risks of health conditions based on changes of the movements relative to the established baseline of the user.

12. The system of claim 11, wherein the control system is further configured to:

receive a second set of sensor data from the at least one movement sensor;

preprocess the second set of sensor data to output a second set of features; and process the second set of features with the updated cyclical individualized movement classifier to output a second movement classification.

13. The system of claim 11, wherein the at least one movement sensor comprises one or more of an accelerometer, a gyroscope, and magnetometer.

14. The system of claim 11, wherein the wearable device is one of a smart watch, smart anklet, and smart band.

15. The system of claim 11, wherein the preset interval spans two minutes before and after the time of the user input confirming the movement classification.

16. The system of claim 11, wherein the threshold percentage is 50 percent, 60 percent, or 70 percent, and the control system determines the start time A and the end time B based on majority agreement.

17. A method comprising:

receiving a set of sensor data comprising data output from at least one movement sensor;

preprocessing the set of sensor data to output a set of features;

processing the set of features with a cyclical individualized movement classifier for a user to output a movement classification, wherein the movement classification comprises one or more of eating, eating with hands, eating with fork and knife, eating with spoon, drinking, lying down, cyclical exercise motions, washing hands, brushing teeth, toilet usage, repeated contact with different anatomic regions, or other cyclical motions that can quantify the time, frequency, and duration of activities of daily living;

providing a notification to the user to confirm the movement classification on an interface;

receiving user input confirming the movement classification;

in response to the user input, generating a plurality of rolling, overlapping time windows over the sensor data within a preset interval before and after a time of the user input, and concurrently processing the plurality of rolling, overlapping time windows in parallel with the cyclical individualized movement classifier;

determining, based at least in part on agreement of at least a threshold percentage of the plurality of rolling, overlapping time windows, a start time A and an end time B of the confirmed movement;

defining AB windows as those rolling, overlapping time windows of the plurality of rolling, overlapping time windows whose ranges fall between the start time A and the end time B;

computing cycle features from the AB windows;

updating, on a device comprising the cyclical individualized movement classifier, the cyclical individualized movement classifier for the user by training the cyclical individualized movement classifier using the confirmed movement classification and the cycle features from the AB windows, to generate an updated cyclical individualized movement classifier for the user;

compiling statistics related to the movement classification;

establishing a baseline of movements based on the statistics, wherein the baseline is specific to the user; and predicting risks of health conditions based on changes of the movements relative to the established baseline of the user.

18. The method of claim 17, wherein the set of features includes one or more of acceleration along an x axis, acceleration along a y axis, acceleration along a z axis, angular velocity along axis x, angular velocity along the y axis, and angular velocity along the z axis, and duration.

19. The method of claim 17, wherein the preprocessing the set of sensor data further comprises segmenting the data into a set of overlapping time windows.

20. The method of claim 17, wherein the threshold percentage is 50 percent, 60 percent, or 70 percent.

* * * * *